(12) United States Patent
Rivera

(10) Patent No.: US 8,225,980 B1
(45) Date of Patent: Jul. 24, 2012

(54) TRUE MULTI-FIRE SURGICAL STAPLER WITH BUTTRESS STRIP

(75) Inventor: John E. Rivera, Woodside, CA (US)

(73) Assignee: Cardica, Inc., Redwood City, CA (US)

( * ) Notice: Subject to any disclaimer, the term of this patent is extended or adjusted under 35 U.S.C. 154(b) by 104 days.

(21) Appl. No.: 12/783,389

(22) Filed: May 19, 2010

Related U.S. Application Data

(60) Provisional application No. 61/183,353, filed on Jun. 2, 2009.

(51) Int. Cl.
*A61B 17/10* (2006.01)

(52) U.S. Cl. .................. 227/177.1; 227/176.1

(58) Field of Classification Search ............ 227/177.1, 227/176.1, 180, 181.1; 606/151, 219; 173/1
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,675,688 A | 7/1972 | Bryan et al. |
| 3,899,914 A | 8/1975 | Akiyama |
| 3,955,581 A | 5/1976 | Spasiano et al. |
| 4,086,926 A | 5/1978 | Green et al. |
| 4,228,895 A | 10/1980 | Larkin |
| 4,275,813 A | 6/1981 | Noiles et al. |
| 4,475,679 A | 10/1984 | Fleury, Jr. |
| 4,589,416 A | 5/1986 | Green |
| 4,633,861 A | 1/1987 | Chow et al. |
| 4,655,222 A | 4/1987 | Florez et al. |
| 4,719,917 A | 1/1988 | Barrows et al. |
| 4,762,260 A | 8/1988 | Richards et al. |
| 4,969,591 A | 11/1990 | Richards et al. |
| 4,978,049 A | 12/1990 | Green |

(Continued)

FOREIGN PATENT DOCUMENTS

EP 1238634 9/1994

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Sameh H. Tawfik
*Assistant Examiner* — Nathaniel Chukwurah
(74) *Attorney, Agent, or Firm* — Brian A. Schar

(57) ABSTRACT

A surgical stapler may include a staple holder; an anvil movable relative to the staple holder; a feeder belt extending into the staple holder; staples frangibly affixed to the feeder belt; and a buttress belt extending onto a surface of the anvil that is oriented toward the staple holder. A surgical method for treating tissue within a patient may include providing a staple holder, an anvil movable relative to the staple holder, a feeder belt extending into the staple holder, staples frangibly affixed to the feeder belt, and a buttress belt extending onto a surface of the anvil that is oriented toward the staple holder; clamping tissue between the anvil and staple holder; deploying staples through the clamped tissue and into the buttress belt, where the staples are connected to said buttress belt as a result; breaking the deployed staples from the feeder belt; and leaving at least a portion of the buttress belt in position against tissue within the patient.

6 Claims, 2 Drawing Sheets

U.S. PATENT DOCUMENTS

| | | | |
|---|---|---|---|
| 5,156,315 A | 10/1992 | Green et al. | |
| 5,170,925 A | 12/1992 | Madden et al. | |
| 5,192,288 A | 3/1993 | Thompson et al. | |
| 5,307,976 A | 5/1994 | Olson et al. | |
| 5,413,272 A | 5/1995 | Green et al. | |
| 5,476,206 A | 12/1995 | Green | |
| 5,547,117 A | 8/1996 | Hamblin et al. | |
| 5,553,765 A | 9/1996 | Knodel et al. | |
| 5,620,289 A | 4/1997 | Curry | |
| 5,630,541 A | 5/1997 | Williamson, IV et al. | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,871,135 A | 2/1999 | Williamson, IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade | |
| 6,391,038 B2 | 5/2002 | Vargas et al. | |
| 6,419,682 B1 | 7/2002 | Appleby et al. | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,147,138 B2 * | 12/2006 | Shelton, IV | 227/176.1 |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0253143 A1 | 11/2006 | Edoga | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0272175 A1 | 11/2008 | Holsten et al. | |
| 2009/0065552 A1 * | 3/2009 | Knodel et al. | 227/180.1 |
| 2009/0206142 A1 * | 8/2009 | Huitema et al. | 227/176.1 |

FOREIGN PATENT DOCUMENTS

| | | |
|---|---|---|
| EP | 1464287 | 10/2004 |
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

"Cardica Microcutter Implant Delivery Device 510(k), Cover Sheet, Table 10.1, "Substantial Equivalence Comparison," and Section 12, "Substantial Equivalence Discussion"", (Oct. 18, 2010).

* cited by examiner

TRUE MULTI-FIRE SURGICAL STAPLER WITH BUTTRESS STRIP

This application claims priority to U.S. Provisional Patent Application Ser. No. 61/183,353, filed on Jun. 2, 2009, which is herein incorporated by reference in its entirety.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. Such an endocutter is described in, for example, U.S. Patent Application Publication No. 2009/0065552, published on Mar. 12, 2009 (the "Endocutter Publication"), which is hereby incorporated by reference herein in its entirety.

BRIEF DESCRIPTION OF THE DRAWINGS

The use of the same reference symbols in different figures indicates similar or identical items.

DETAILED DESCRIPTION

Figure 1:
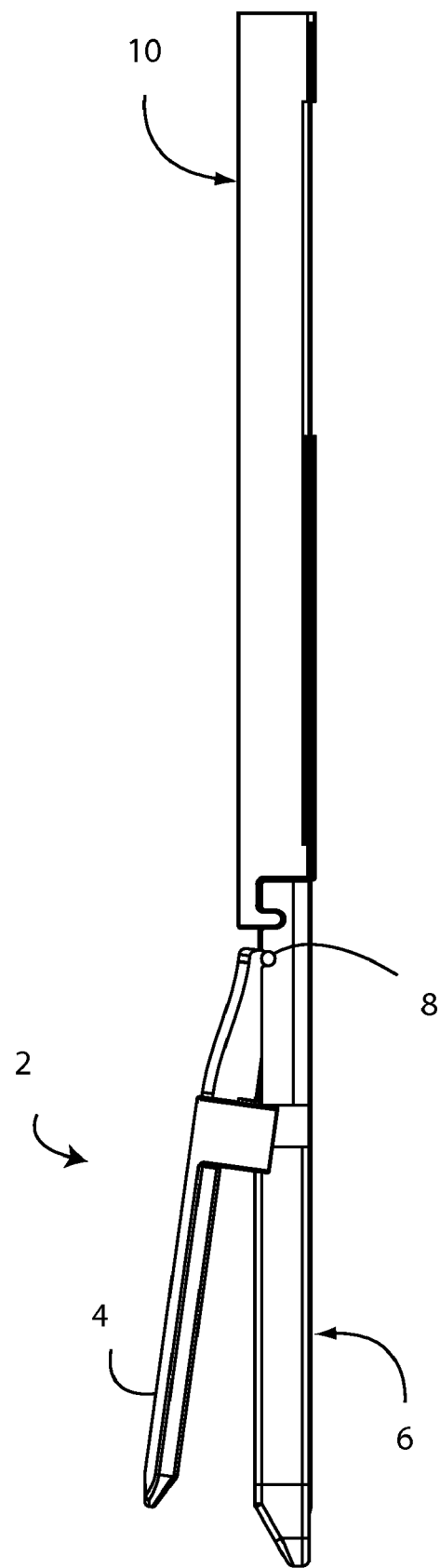
FIG. 1 is a side view of an exemplary end effector with a staple holder and an anvil.

Referring to FIG. 1, an end effector 2 of a surgical stapler may include an anvil 4 connected to a staple holder 6. At least one of the anvil 4 and staple holder 6 is movable relative to the other. As one example, the anvil 4 is pivotally connected to the staple holder 6 at a pivot point 8, such that the anvil 4 can pivot from an open position (as seen in FIG. 1) to a closed position and back again. The end effector 2 may be connected to the distal end of a shaft 10 or other structure. The end effector 2 and shaft 10 may be configured as set forth in the Endocutter Publication, with the exception of any specific differences identified herein.

Figure 2:
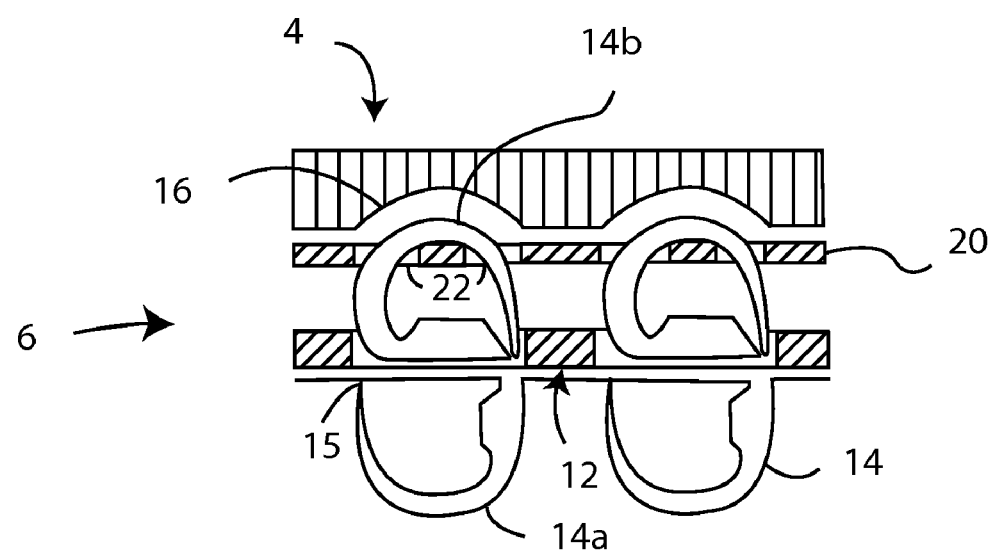
FIG. 2 is a detail cutaway side view of an endocutter with a feeder belt and staples in a staple holder (showing the staples in two separate positions in time), and a buttress strip in an anvil.

Referring also to FIG. 2, the staple holder 6 may be configured to hold at least part of at least one feeder belt 12 to which a plurality of staples 14 that are fixed to and frangibly separable therefrom. The feeder belt 12 and staples 14 may be substantially as set forth in the Endocutter Publication. Staple forming pockets 16 may be defined in the surface of the anvil 4 that faces toward the staple holder 6. In this way, as staples 14 are ejected from the staple holder 6, those staples 14 encounter corresponding staple forming pockets 16 on the surface of the anvil 4, urging those staples 14 to deform and close.

A separate buttress belt 20 may be provided in association with the anvil 4. The buttress belt 20 may be configured substantially in the same manner as the feeder belt 12, but without staples attached. Further, the buttress belt 20 may include apertures 22 defined therethrough. The apertures 22 in the buttress belt 20 are positioned relative to the feeder belt 12 such that, during deployment of the staples 14 from a first position 14a to the closed position 14b, the free end 15 of at least one staple 14 enters a corresponding aperture 22 in the buttress belt 20, moves above the buttress belt 20, then moves downward into and through another aperture 22 in the buttress belt 20. After the staple 14 is completely closed, it is locked onto the buttress belt 20, providing increased clamping strength in tissue.

The buttress belt 20 may be configured in any manner to hold staples 14 individually or in groups. As one example, the buttress belt 20 may be perforated, breakable or separable such that at least one staple 14 and its corresponding portion of the buttress belt 20 to which it is connected is separable from a remaining portion of the buttress belt 20. As another example, the buttress belt 20 holds two or more staples, and is separably connected to a more-proximal segment of the buttress belt 20. As another example, instead of the buttress belt 20, a strip with similar characteristics is utilized, where that strip is loaded onto the anvil 4, then replaced manually after it is used prior to the next firing. As another example, the buttress belt 20 may be fabricated from flexible buttress material, or from a different material than the feeder belt 12.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:

1. A surgical method for treating tissue within a patient; comprising:
    possessing a staple holder, an anvil movable relative to said staple holder, a feeder belt extending into said staple holder, a plurality of staples frangibly affixed to said feeder belt, and a buttress belt extending onto a surface of said anvil that is oriented toward said staple holder, wherein said buttress belt includes a plurality of apertures defined therein;
    clamping tissue between said anvil and said staple holder;
    deploying a plurality of said staples through the tissue clamped between said anvil and said staple holder by urging an end of at least one said staple through a first said aperture defined in said buttress belt, wherein said staples are connected to said buttress belt;

breaking said deployed plurality of said staples from said feeder belt; and leaving at least a portion of said buttress belt in position against tissue within the patient.

2. The surgical method of claim 1, wherein said leaving includes separating said portion of said buttress belt from a remainder of said buttress belt at a perforation.

3. The surgical method of claim 1, further comprising advancing both said feeder belt and said buttress belt, after which a different plurality of said staples is located within said staple holder.

4. The surgical method of claim 3, wherein said advancing is performed while said staple holder and said anvil are located inside the patient.

5. The surgical method of claim 1, wherein said deploying further includes bending at least one said staple and urging said end of said staple through a second said aperture after first urging said end of said staple through said first said aperture.

6. The surgical method of claim 1, further comprising manually replacing said buttress belt on said anvil after said leaving.

\* \* \* \* \*